(12) United States Patent
Smith et al.

(10) Patent No.: US 11,285,328 B2
(45) Date of Patent: Mar. 29, 2022

(54) ANTENNA ASSEMBLIES FOR USE WITH TRANSCUTANEOUSLY POWERED MEDICAL IMPLANTS

(71) Applicant: ADVANCED BIONICS AG, Staefa (CH)

(72) Inventors: James George Elcoate Smith, Santa Clarita, CA (US); Uli Gommel, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 153 days.

(21) Appl. No.: 16/775,209

(22) Filed: Jan. 28, 2020

(65) Prior Publication Data

US 2021/0234265 A1    Jul. 29, 2021

(51) Int. Cl.
| | |
|---|---|
| *H01Q 1/52* | (2006.01) |
| *A61N 1/372* | (2006.01) |
| *A61N 1/36* | (2006.01) |
| *H01Q 7/00* | (2006.01) |
| *A61N 1/08* | (2006.01) |
| *A61N 1/378* | (2006.01) |

(52) U.S. Cl.
CPC ........... *A61N 1/37229* (2013.01); *A61N 1/08* (2013.01); *A61N 1/36038* (2017.08); *H01Q 1/526* (2013.01); *H01Q 7/00* (2013.01); *A61N 1/3787* (2013.01)

(58) Field of Classification Search
CPC .... A61N 1/08; A61N 1/3787; A61N 1/37229; A61N 1/36038; H04B 5/0025; H01Q 7/00; H01Q 1/526
See application file for complete search history.

(56) References Cited

U.S. PATENT DOCUMENTS

| | | | |
|---|---|---|---|
| 3,753,203 A * | 8/1973 | Link | H01R 13/53 |
| | | | 439/95 |
| 3,870,987 A * | 3/1975 | Wiley | H01B 3/445 |
| | | | 338/214 |
| 5,385,578 A | 1/1995 | Bush et al. | |
| 5,876,326 A | 3/1999 | Takamura et al. | |
| 6,515,632 B1 | 2/2003 | McLean | |
| 6,542,777 B1 | 4/2003 | Griffith et al. | |
| 7,191,007 B2 | 3/2007 | Desai et al. | |
| 7,876,282 B2 | 1/2011 | Keilman et al. | |

(Continued)

FOREIGN PATENT DOCUMENTS

| | | |
|---|---|---|
| WO | WO 2012/047550 A1 | 4/2012 |
| WO | WO 2015021359 A1 | 2/2015 |

(Continued)

OTHER PUBLICATIONS

Giancoli, Douglas C, Resistivity Table, Physics, 4th ed., Prentice Hall (1995) (Year: 1995).*

(Continued)

*Primary Examiner* — Catherine M Voorhees
(74) *Attorney, Agent, or Firm* — Henricks Slavin LLP (57) ABSTRACT

An antenna assembly for use with a medical implant includes an antenna and an electromagnetic shield. At least one of the antenna and the shield includes electrically conductive conductor that defines a conductor resistance and an electrically conductive sheath, over electrically conductive conductor, that defines a sheath resistance that is greater than the conductor resistance.

18 Claims, 6 Drawing Sheets

(56) References Cited

U.S. PATENT DOCUMENTS

| | | |
|---|---|---|
| 8,781,606 B2 | 7/2014 | Keilman et al. |
| 8,825,171 B1 | 9/2014 | Thenuwara et al. |
| 10,543,369 B2 | 1/2020 | Nyberg, II et al. |
| 11,185,702 B2 | 11/2021 | Davis et al. |
| 2005/0134519 A1 | 6/2005 | Fukano et al. |
| 2006/0038730 A1 | 2/2006 | Parsche |
| 2008/0051854 A1 | 2/2008 | Bulkes et al. |
| 2009/0248105 A1 | 10/2009 | Keilman et al. |
| 2010/0046779 A1 | 2/2010 | Crawford et al. |
| 2011/0009925 A1 | 1/2011 | Leigh et al. |
| 2012/0089202 A1 | 4/2012 | Staller |
| 2014/0197832 A1 | 7/2014 | Driesel et al. |
| 2014/0314264 A1 | 10/2014 | Meskens et al. |
| 2015/0025613 A1 | 1/2015 | Nyberg, II et al. |
| 2018/0071542 A1 | 3/2018 | Nyberg, II et al. |
| 2019/0009096 A1* | 1/2019 | Davis ............... A61N 1/375 |
| 2019/0334230 A1 | 10/2019 | Jesme et al. |

FOREIGN PATENT DOCUMENTS

| | | |
|---|---|---|
| WO | WO 2016198426 A1 | 12/2016 |
| WO | WO 2017218619 A1 | 12/2017 |

OTHER PUBLICATIONS

Litz wire. In Wikipedia. Retrieved Apr. 17, 2015, from https://en.wikipedia.org/wiki/Litz_wire.

Litz Wire Types and Constructions. Retrieved Apr. 17, 2015, from www.newenglandwire.com.

Schaffer. *General Characteristics of DFT® Composite Wire*. Fort Wayne Metals Research Products Corporation. 2002.

* cited by examiner

| | |
|---|---|
| 102 housing | 302 housing |
| 104 processor | 304 connector |
| 106 cochlear lead | 306 microphone |
| 108 antenna | 308 antenna |
| 122 magnet | 310 magnet |

ANTENNA ASSEMBLIES FOR USE WITH TRANSCUTANEOUSLY POWERED MEDICAL IMPLANTS

BACKGROUND

1. Field

The present disclosure relates generally to transcutaneously powered medical implants.

2. Description of the Related Art

Inductive links are commonly used to transmit power and data to implanted medical devices such as, for example, prosthetic devices including cochlear implants and retinal implants, cardiac pacemakers, implantable defibrillators, recording devices, and neuromuscular stimulators. The implanted devices include (or are connected to) an internal antenna coil, and an external antenna coil is positioned over the internal antenna coil. Power and in some instances data is supplied to the implanted devices by way of the inductive link between the antenna coils.

In the exemplary context of implantable cochlear stimulation ("ICS") systems, which include an external sound processor as well as a cochlear implant with an electrode array within the cochlea, the external antenna coil may be carried by a headpiece that is connected to the external sound processor. The sound processor transmits power and stimulation data (e.g., a pulse sequence having varying pulse widths and/or amplitudes) through a power modulation scheme to the antenna coil of the cochlear implant by way of an inductive link. One conventional implant antenna coil is a three turn inductor that includes a conductor formed from gold, platinum or titanium wire within a non-conductive carrier. The conductor also may include biocompatible multi-wire metal cables formed from gold, platinum or titanium wire. Electrical stimulation current is then applied to varying electrode combinations in the electrode array to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics Harmony™ BTE sound processor, the Advanced Bionics Naída CI Q Series BTE sound processors and the Advanced Bionics Neptune™ body worn sound processor.

In some antenna assemblies, an electromagnetic shield is located around the antenna coil in order to reduce noise and undesirable alteration of the characteristics of the antenna coil caused by external objects. One exemplary method of forming an electromagnetic shield involves, among other things, overmolding a silicone shield guide onto the antenna coil, anchoring shield wires (such as platinum wires) at two adjacent locations, and carefully wrapping the shield wires around the shield guide (and antenna coil). Exemplary cochlear implants with electromagnetic shields are illustrated and described in U.S. Pat. No. 8,825,171, U.S. Pat. Pub. No. 2015/0025613 and WO Pub. No. 2016171833.

The present inventors have determined that conventional antenna assemblies are susceptible to improvement. For example, one issue associated with conventional antenna assemblies is impact-related damage to the antenna and shield wires. A break (or a plurality of breaks) in the antenna and/or shield wires can prevent the antenna assembly from functioning properly and/or cause a loss of transmission efficiency (and corresponding excessive battery drain), thereby preventing communication to and from the associated cochlear implant and necessitating replacement of the cochlear implant. One conventional method of reducing the likelihood of antenna and/or shield wire breakage is to add a polyethylene fiber that follows the turns of the inductor and is also covered by the shield guide. The present inventors have determined that although the use of a polyethylene fiber reduces the likelihood that the antenna wire will break, it would be desirable to eliminate the manufacturing costs associated with the addition of the polyethylene fiber. The present inventors have also determined that it would be desirable to reduce the likelihood that breaks in the antenna wire and/or shield wires, should they occur, will prevent the antenna assembly from functioning properly.

SUMMARY

An antenna assembly for use with a medical implant includes an antenna that defines at least one turn and an electromagnetic shield that extends around the antenna. In at least some implementations, the antenna may include an electrically conductive antenna conductor that defines an antenna conductor resistance and an electrically conductive antenna sheath, over electrically conductive antenna conductor, that defines an antenna sheath resistance that is greater than the antenna conductor resistance. Alternatively, or in addition, the electromagnetic shield may include an electrically conductive shield conductor that defines a shield conductor resistance and an electrically conductive shield sheath, over electrically conductive shield conductor, that defines a shield sheath resistance that is greater than the shield conductor resistance. The present inventions also include implantable medical devices, such as cochlear implants, with such an antenna assembly.

There are a number of advantages associated with such antenna assemblies. For example, in those instances where a conductor is broken, and adjacent portions thereof are separated by a gap, current flowing through the conductor will flow into the conductive sheath, around the gap, and then back into the conductor, as this is the path of least resistance in the location of the gap-forming break. Accordingly, even in those instances where there is one or more breaks in the antenna conductor and/or the shield conductor, the antenna assembly will continue to function properly.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in a wide variety of systems including, but not limited to, those that provide sound (i.e., either sound or a perception of sound) to the hearing impaired. One example of such a system is an ICS system where an external sound processor communicates with a cochlear implant and, accordingly, the present inventions may be discussed in the context of cochlear implants. The present inventions are not, however, so limited, and have application in other systems where, for example, power and data are transmitted to an implanted medical device by way of an inductive link.

Figure 1:
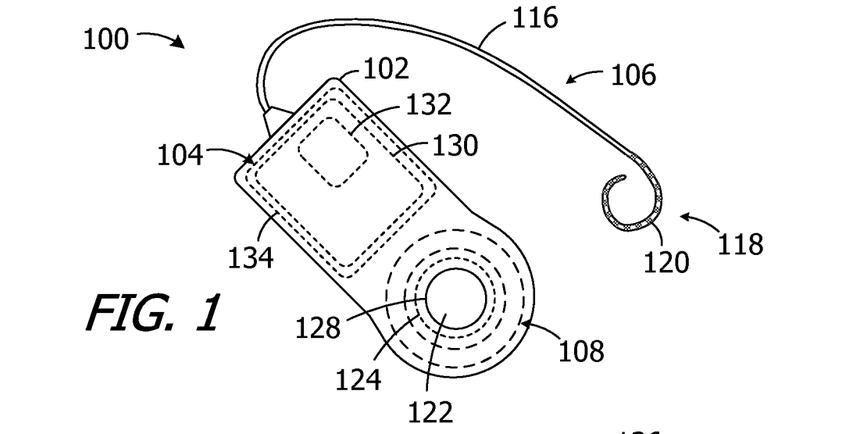
FIG. 1 is a top view of an exemplary implantable cochlear stimulator in accordance with one embodiment of a present invention.
Figure 2:
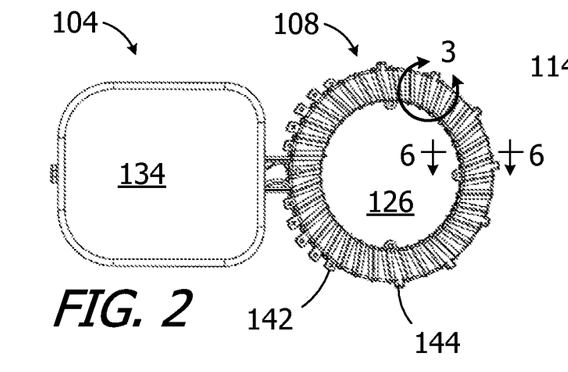
FIG. 2 is a top view of a portion of the implantable cochlear stimulator illustrated in FIG. 1.
Figure 3:
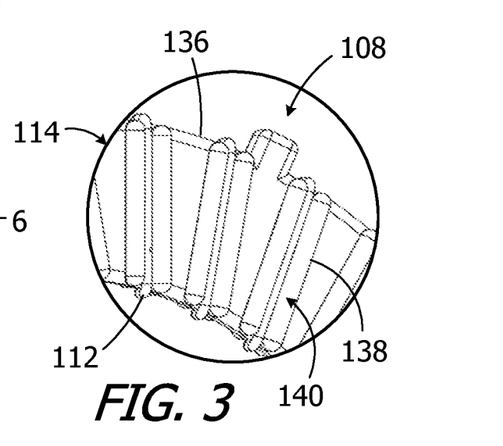
FIG. 3 is an enlarged view of a portion of FIG. 2.

One example of a cochlear implant (or "implantable cochlear stimulator") is the cochlear implant 100 illustrated in FIG. 1. Referring also to FIGS. 2-5, the cochlear implant 100 includes a flexible housing 102 formed from a silicone elastomer or other suitable material, a processor assembly 104, a cochlear lead 106, and an antenna assembly 108 with an antenna coil (or "antenna") 110, an electromagnetic shield (or "shield") 112 and an electrically non-conductive overmolded shield guide ("shield guide") 114 between the antenna and the shield. The antenna 110 may be used to receive data and power by way of an external antenna that is associated with, for example, a sound processor unit, while the electromagnetic shield 112 (which has a disconnection 113) functions in a manner similar to the electromagnetic shields in other hearing related devices. The cochlear lead 106 may include a flexible body 116, an electrode array 118 at one end of the flexible body, and a plurality of wires (not shown) that extend through the flexible body from the electrodes 120 (e.g., platinum electrodes) in the array 118 to the other end of the flexible body. A magnet 122 is located within a region encircled by the antenna assembly 108 (e.g., within an internal pocket 124 defined by the housing 102). The magnet 122 ensures that an external antenna will be properly positioned relative to the antenna 110. The antenna assembly 108, as well as the other antenna assemblies described below, have an overall annular shape with an open central region 126 to accommodate the magnet 122 and magnet pocket 124. An opening 128 allows the magnet 122 to be removed from the internal pocket 124 if necessary. The exemplary processor assembly 104, which is connected to the electrode array 118 and antenna 110, includes a printed circuit board 130 with a stimulation processor 132 that is located within a hermetically sealed case 134. The case 134 may be formed from titanium or other suitable materials. The stimulation processor 132 converts the stimulation data into stimulation signals that are transmitted to the cochlea by way of the electrodes 120 of the electrode array 118.

Referring more specifically to FIGS. 2-5, the exemplary electrically non-conductive shield guide 114 includes an annular main body 136 and a plurality of protrusions 138. The antenna 110 is located within the annular main body 136, while the protrusions 138 define slots 140 for the shield 112. The shield guide 114 may also include tabs 142 with apertures and tabs 144 without apertures. The tabs 142 and 144 center the shield guide within the mold during subsequent overmolding, thereby ensuring that the antenna 110 will be centered within the mold. In other implementations, such as that illustrated in FIG. 18, the tabs may be omitted. Suitable electrically non-conductive materials for the shield guide 114 include, but are not limited to, silicone rubber and other elastomeric materials.

Figure 4:
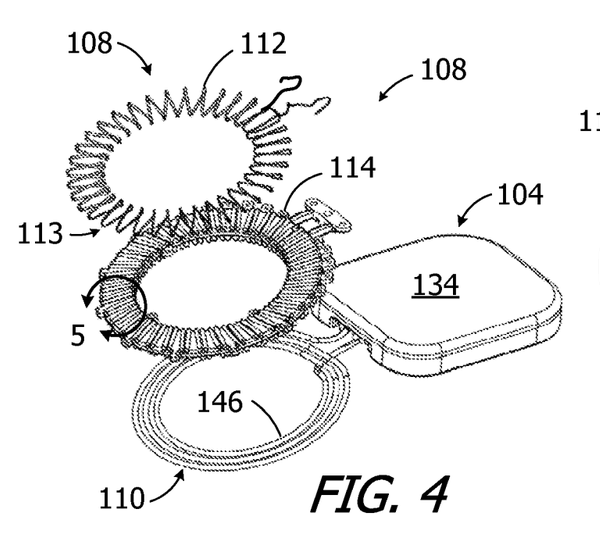
FIG. 4 is an exploded view of a portion of the implantable cochlear stimulator illustrated in FIG. 1.
Figure 5:
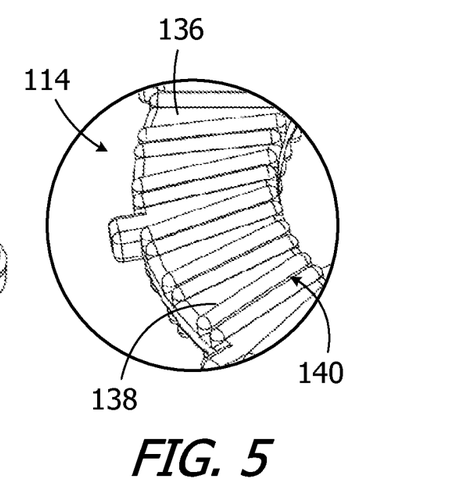
FIG. 5 is an enlarged view of a portion of FIG. 4.
Figure 6:
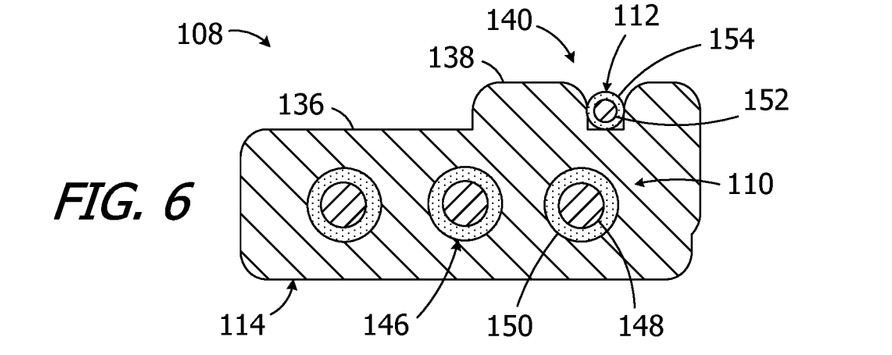
FIG. 6 is a section view taken along line 6-6 in FIG. 2.

Turning to FIGS. 4 and 6, the exemplary antenna 110 is formed by an inductor assembly 146 that includes an electrically conductive metallic conductor 148 (e.g., a gold wire) that is located within an electrically conductive sheath 150. The conductive sheath 150 has a higher electrical resistance than the metallic conductor 148 and, as a result, current flowing through the metallic conductor 148 will remain within the metallic conductor under normal operating conditions. For example, the electrical resistance of the conductive sheath 150 may be at least 10% greater than the electrical resistance of the metallic conductor 148, and is 10 to 30% greater than the electrical resistance of the metallic conductor 148 in some implementations, and is 30% greater in one specific implementation. The inductor assembly 146 defines one or more turns (or "loops" or "windings"), the number of which is determined by the intended application, and there are three turns in the illustrated embodiment. Also, although the exemplary conductor 148 is a single solid wire, other conductors may be employed, as is discussed below. The exemplary shield 112 is formed from an electrically conductive metallic conductor 152 (e.g., a platinum wire) that is located within a conductive sheath 154 that has a higher electrical resistance than the metallic conductor 152. For example, the electrical resistance of the conductive sheath 154 may be 10 to 30% greater than the electrical resistance of the metallic conductor 152, and is at least 70% greater in some implementations. Current flowing through the metallic conductor 152 will remain within the metallic conductor under normal operating conditions.

The conductive sheaths 150 and 154 may be formed from an electrically non-conductive elastomer (e.g., silicone) that is heavily dosed with electrically conductive nano-particles and/or nano-fibers (e.g., nano-particles and nano-fibers formed from noble metals such as platinum or gold, Graphene or any other any biocompatible conductive material) or carbon nanotubes. Examples of such electrically conductive elastomers are disclosed in WO2016/198426 and WO2019/211754 and are sold under the tradename FlexOne by nanoleq AG of Zurich, Switzerland. In at least some implementations, the conductive sheaths 150 and 154 may be 5-30% electrically conductive nano-particles and/or nano-fibers by weight or by volume. Briefly, the conductive sheaths 150 and 154 allow current to bypass breaks in the metallic conductors 148 and 152 as is described in greater detail below with reference to FIGS. 8-10.

Figure 7:
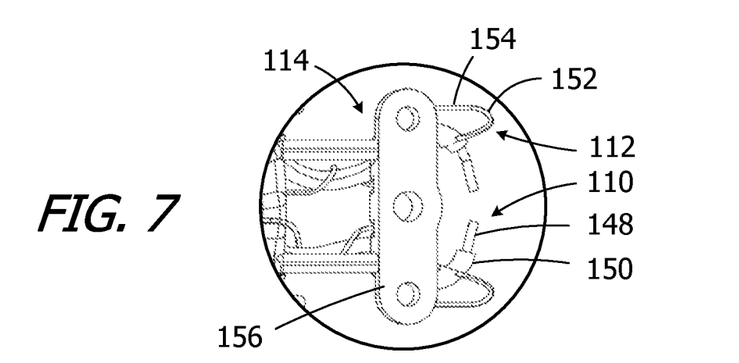
FIG. 7 is a bottom view of a portion of the implantable cochlear stimulator illustrated in FIG. 1.

As illustrated in FIG. 7, the exemplary shield guide 114 also includes a wire holder 156 that is used to hold the ends of the antenna 110 and shield 112 at predetermined locations, thereby facilitating connection to the appropriate portions to the processor assembly 104. To that end, the ends of conductive metallic conductor 148 of the antenna 110 are exposed for connection to the processor assembly, as are the ends of the metallic conductor 152 of the shield 112.

Figure 8:
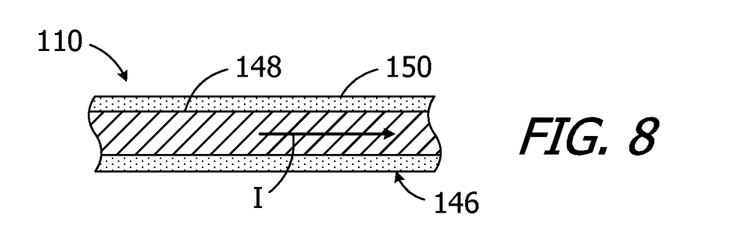
FIG. 8 is a section view of a portion of the implantable cochlear stimulator illustrated in FIG. 1.
Figure 9:
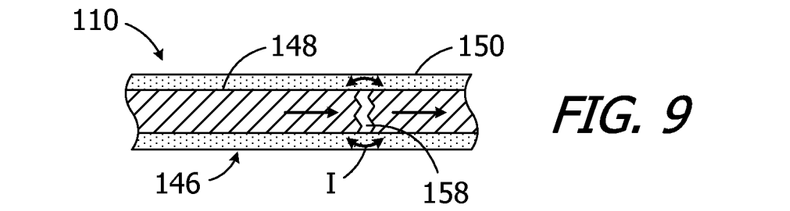
FIG. 9 is a section view of a portion of the implantable cochlear stimulator illustrated in FIG. 1 with the conductor in a broken state.

Turning to FIG. 8, in the absence of a break, current I flowing through the inductor assembly 146 of the antenna 110 will remain within the metallic conductor 148 due the higher electrical resistance of the conductive sheath 150. The conductive sheath 150 will remain intact, due to elasticity of the silicone (or other elastomeric material), when the metallic conductor is broken and adjacent portions thereof are separated by a gap 158 (FIG. 9). Here, the current I flowing through the metallic conductor 148 will flow into the conductive sheath 150, around the gap 158, and then back into the metallic conductor 148, as this is the path of least resistance in the location of the gap-forming break in the metallic conductor. Similarly, current flowing through an unbroken shield 112 will remain within the metallic conductor 152 due the higher electrical resistance of the conductive sheath 154. In those instances where the metallic conductor 152 is broken, and adjacent portions thereof are separated by a gap 160 (FIG. 10), the current I flowing through the metallic conductor 152 will flow into the conductive sheath 154, around the gap 160, and then back into the metallic conductor 152, as this is the path of least resistance in the location of the gap-forming break in the metallic conductor. Accordingly, even in those instances where there is one or more breaks in the antenna conductor and/or the shield conductor, the antenna assembly 108 will continue to function properly.

Figure 11:
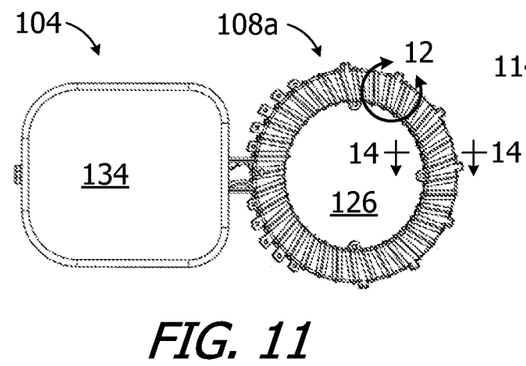
FIG. 11 is a top view of a portion of an implantable cochlear stimulator in accordance with one embodiment of a present invention.
Figure 12:
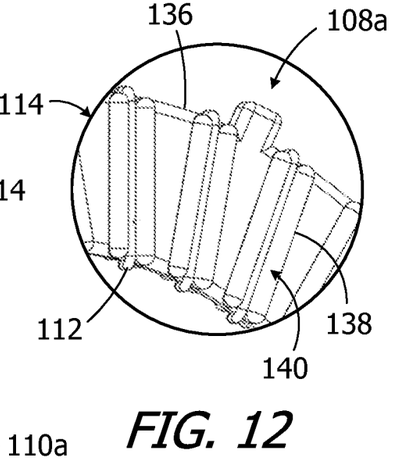
FIG. 12 is an enlarged view of a portion of FIG. 11.
Figure 13:
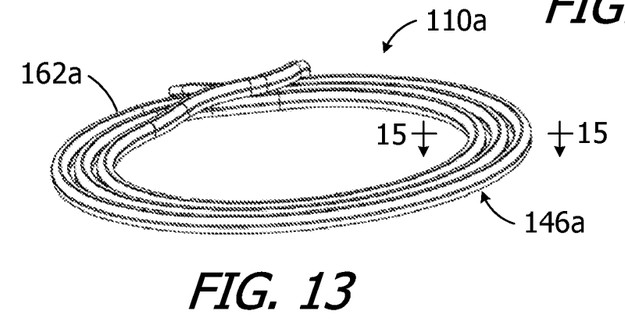
FIG. 13 is perspective view of a portion of the antenna assembly illustrated in FIG. 11.
Figure 14:
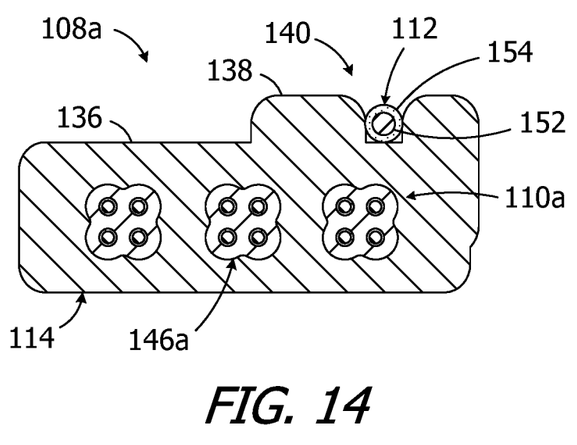
FIG. 14 is a section view taken along line 14-14 in FIG. 11.
Figure 15:
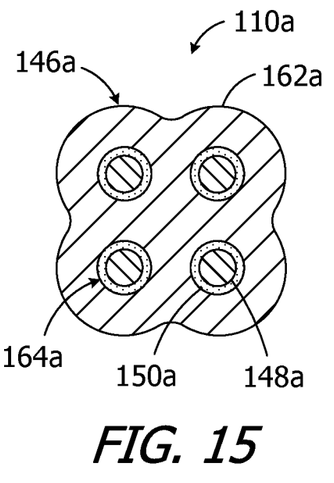
FIG. 15 is a section view of a single turn taken along line 15-15 in FIG. 14.

Another exemplary antenna assembly is generally represented by reference numeral 108a in FIG. 11. The exemplary antenna assembly 108a, which may be connected to the processor assembly 104 and incorporated into a cochlear implant such as the cochlear implant 100 illustrated in FIG. 1, is substantially similar to antenna assembly 108 and similar elements are represented by similar reference numerals. Here, however, and referring also to FIGS. 12-15, the antenna assembly 108a includes an antenna 110a that is formed by an inductor assembly 146a with a plurality of electrically conductive metallic conductors 148a (e.g., a plurality of gold wires) that are each located within a respective electrically conductive sheath 150a that has a higher electrical resistance than the associated metallic conductor 148a. The metallic conductors 148a and sheaths 150a are located within a carrier 162a that maintains the position of the metallic conductors in predetermined positions relative to one another. The inductor assembly 146a defines one or more turns (or "loops" or "windings"), the number of which is determined by the intended application, and there are three turns in the illustrated embodiment. The exemplary carrier 162a includes a lumen 164a for each one of the sheath covered metallic conductors 148a. The carrier 162a may be formed from a dense elastomeric electrically non-conductive material such as silicone rubber.

The exemplary antenna assembly 108a also includes the above-described electromagnetic shield 112 and electrically non-conductive overmolded shield guide 114 between the antenna 110a and the shield. The antenna 110a is located within the annular main body 136 of the shield guide 114, while the shield 112 is wound around the shield guide using the shield guide slots 140.

Figure 10:
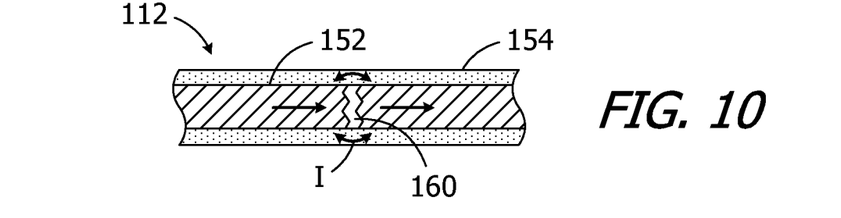
FIG. 10 is a section view of a portion of the implantable cochlear stimulator illustrated in FIG. 1 with the conductor in a broken state.

As discussed in greater detail above with reference to FIGS. 9 and 10, current I flowing through the inductor assembly 146a of the antenna 110a will remain within the metallic conductors 148a, absent a gap-forming conductor break, due the higher electrical resistance of the conductive sheaths 150a. When a conductor break occurs, the associated conductive sheath 150a will remain intact and current flowing through the broken metallic conductor 148a will flow into the conductive sheath 150a, around the gap, and then back into the metallic conductor 148a. Current will flow through an unbroken shield 112, as well as a broken shield 112, in the manner described above with reference to FIG. 10.

Accordingly, even in those instances where there is a break in the antenna conductor and/or the shield conductor, the antenna assembly 108a will continue to function properly.

The exemplary conductors 148a are formed from a single conductive wire. In other implementations, the conductors may be in the form of multi-wire cables. To that end, and turning to FIGS. 16 and 17, the exemplary antenna 110b is substantially similar to antenna 110a and may be incorporated into antenna assemblies and cochlear implants in the same manner as antennas 110 and 110a. The antenna 110b is formed by an inductor assembly 146b with a plurality of electrically conductive metallic conductors 148b and an electrically conductive sheath 150b that has a higher electrical resistance than the metallic conductors 148b. The metallic conductors 148b are multi-wire cables (sometimes referred to as "Litz wires"), and each wire 166 may be a drawn filled tubing ("DFT") that includes an outer tube 168 (e.g., an MP35N® nickel alloy tube) filled with an inner core 170 (e.g., a silver or silver alloy core). DFT is a registered trademark of Fort Wayne Metals Research Products Corp. and MP35N is a registered trademark of SPS Technologies. In the illustrated embodiment, the conductors 148b include seven wires 166 that are arranged in a hexagonal formation where six of the wires are twisted around a center wire. The ends of the metallic conductors 148b are exposed so as to facilitate connection to the circuitry within the processor assembly 104 in the manner described above. The material for the conductive sheaths 150b may be applied to the conductors 148b by extrusion molding.

Figure 16:
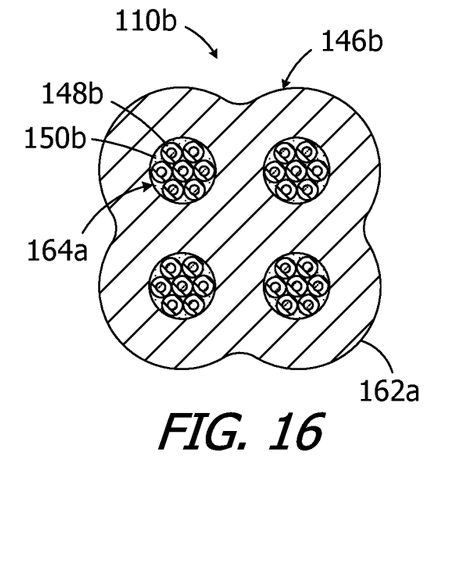
FIGS. 16 and 17 are section views of a portion of an implantable cochlear stimulator in accordance with one embodiment of a present invention.
Figure 17:
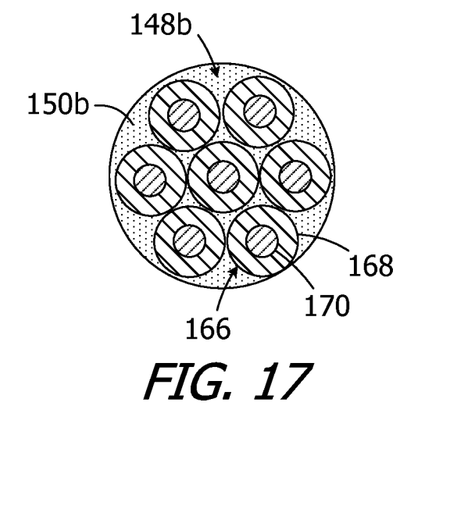

The metallic conductors 148b, with respective conductive sheaths 150b applied thereover, are located within a carrier 162a (described above) that maintains the position of the metallic conductors relative to one another. The inductor assembly 146b defines one or more turns, the number of which is determined by the intended application, and there are three turns in the illustrated embodiment.

As discussed in greater detail above with reference to FIGS. 9 and 10, current I flowing through the inductor assembly 146b of the antenna 110b will remain within the metallic conductors 148b, absent a gap-forming conductor break, due the higher electrical resistance of the conductive sheaths 150b. When a conductor break occurs, the associated conductive sheath 150b will remain intact and current flowing through the metallic conductor 148b will flow into the conductive sheath 150b, around the gap, and then back into the metallic conductor 148b. Accordingly, even in those instances where there is a break in the antenna conductor, an antenna assembly that includes antenna 110b will continue to function properly.

Figure 18:
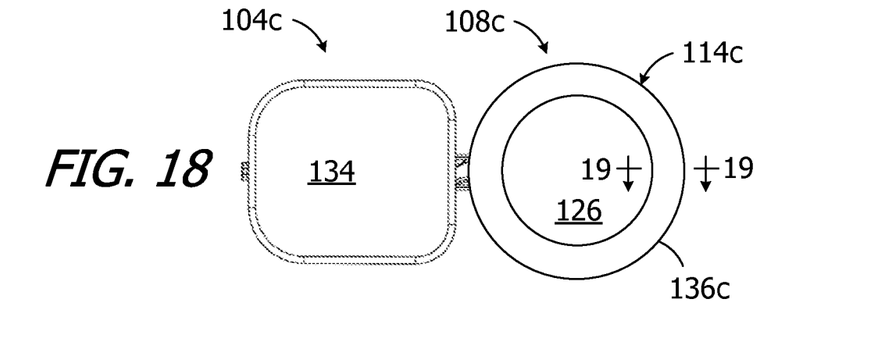
FIG. 18 is a top view of a portion of an implantable cochlear stimulator in accordance with one embodiment of a present invention.
Figure 19:
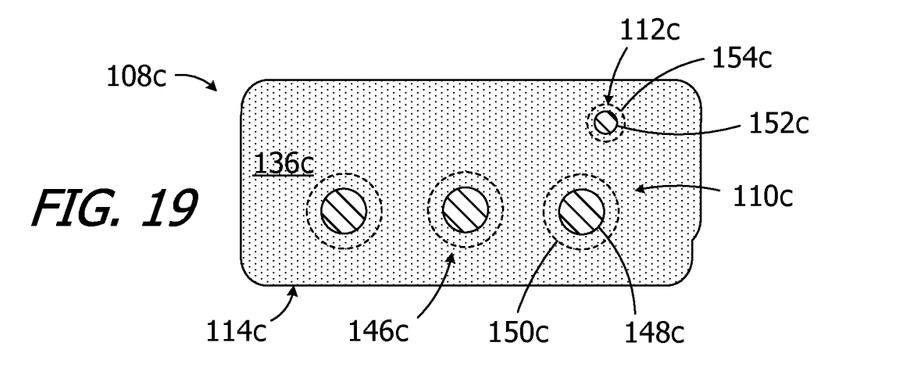
FIG. 19 is a section view taken along line 19-19 in FIG. 18.

Another exemplary antenna assembly is generally represented by reference numeral 108c in FIGS. 18 and 19. The exemplary antenna assembly 108c, which may be connected to the processor assembly 104 and incorporated into a cochlear implant such as the cochlear implant 100 illustrated in FIG. 1, is substantially similar to antenna assembly 108 and similar elements are represented by similar reference numerals. For example, the antenna assembly 108c includes an antenna 110c, which that is formed by an inductor assembly 146c that includes an electrically conductive metallic conductor 148c (e.g., a gold wire), as well as a shield 112c includes an electrically conductive metallic conductor 152c (e.g., a platinum wire). Here, however, the metallic conductors 148c and 152c are located within a conductive structure 151c that has a higher electrical resistance than the metallic conductors 148c and 152c. The conductive structure 151c has respective portions (shown in dash lines) that function as an electrically conductive sheath 150c for the inductor assembly metallic conductor 148c, as a shield guide 114c for the shield 112c, and as a conductive sheath 154c for the shield metallic conductor 152c.

Figure 20:
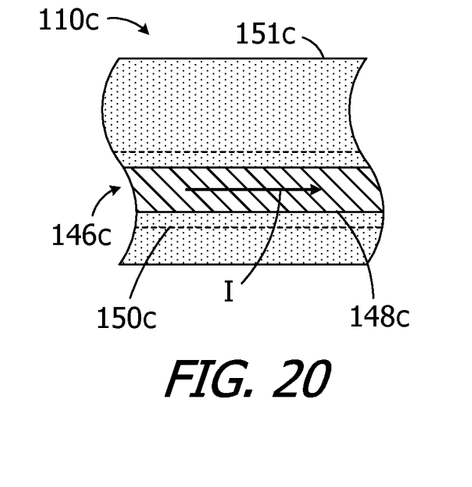
FIG. 20 is a section view of a portion of the antenna assembly illustrated in FIG. 18.
Figure 21:
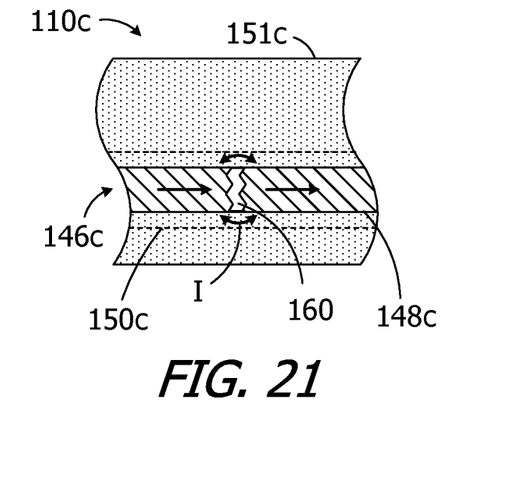
FIG. 21 is a section view of a portion of the antenna assembly illustrated in FIG. 18 with the conductor in a broken state.

As illustrated in FIGS. 20 and 21, current I flowing through the inductor assembly 146c of the antenna 110c will remain within the metallic conductors 148c, absent a gap-forming conductor break, due the higher electrical resistance of the portion of the conductive structure 151c that forms the conductive sheath 150c. When a conductor break occurs, the associated conductive sheath 150c will remain intact and current flowing through the metallic conductor 148c will flow into the conductive sheath 150c, around the gap 160, and then back into the metallic conductor 148c. Current will flow through an unbroken shield 112c, as well as a broken shield 112c, in the manner described above with reference to FIG. 10. Accordingly, even in those instances where there is a break in the antenna conductor and/or the shield conductor, an antenna assembly that includes antenna 110c will continue to function properly.

Figure 22:
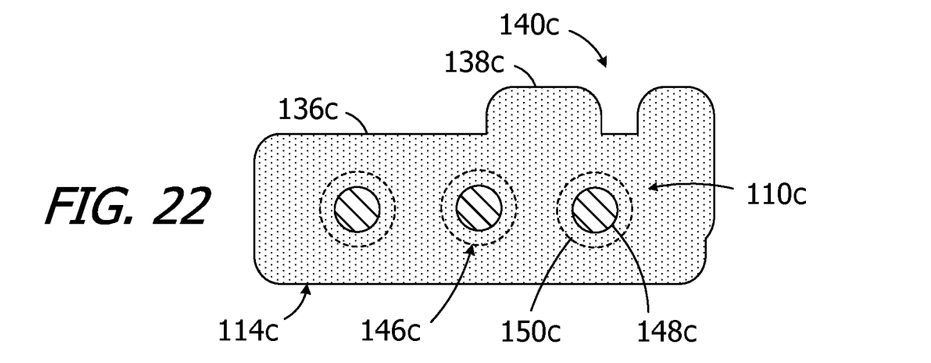
FIGS. 22 and 23 are section views of portions of a process in accordance with one embodiment of a present invention.
Figure 23:
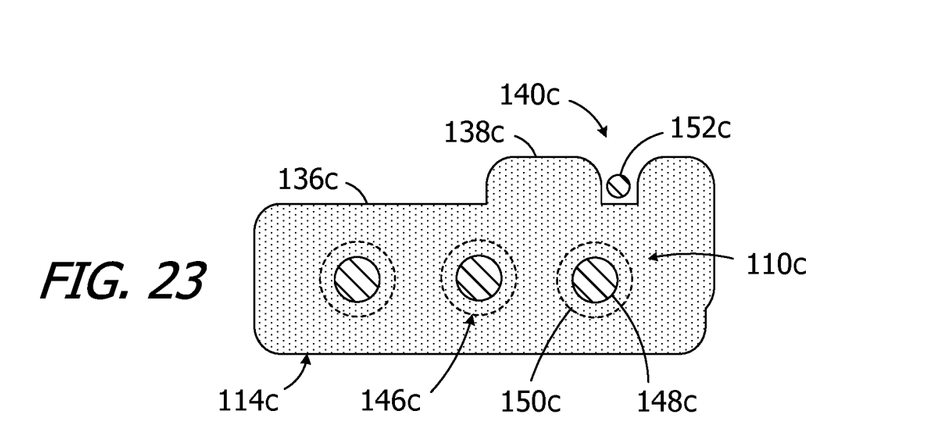

In one exemplary manufacturing method, the inductor assembly 146c may be molded into the shield guide 114c (FIG. 22) that is formed from conductive material that has a higher electrical resistance than both the metallic conductor 148c and the shield metallic conductor 152c. The shield metallic conductor 152c may then the be wound around the shield guide 114c by way of the protrusions 138c and slots 140c (FIG. 23). Conductive material that has a higher electrical resistance than at least the shield metallic conductor 152c may be overmolded onto the wire guide 114c to enclose the metallic conductor 152c, thereby completing the shield 112c (FIG. 19). The material overmolded onto the wire guide 114c may be the same material that was used to form wire guide 114c, or a different material.

Figure 24:
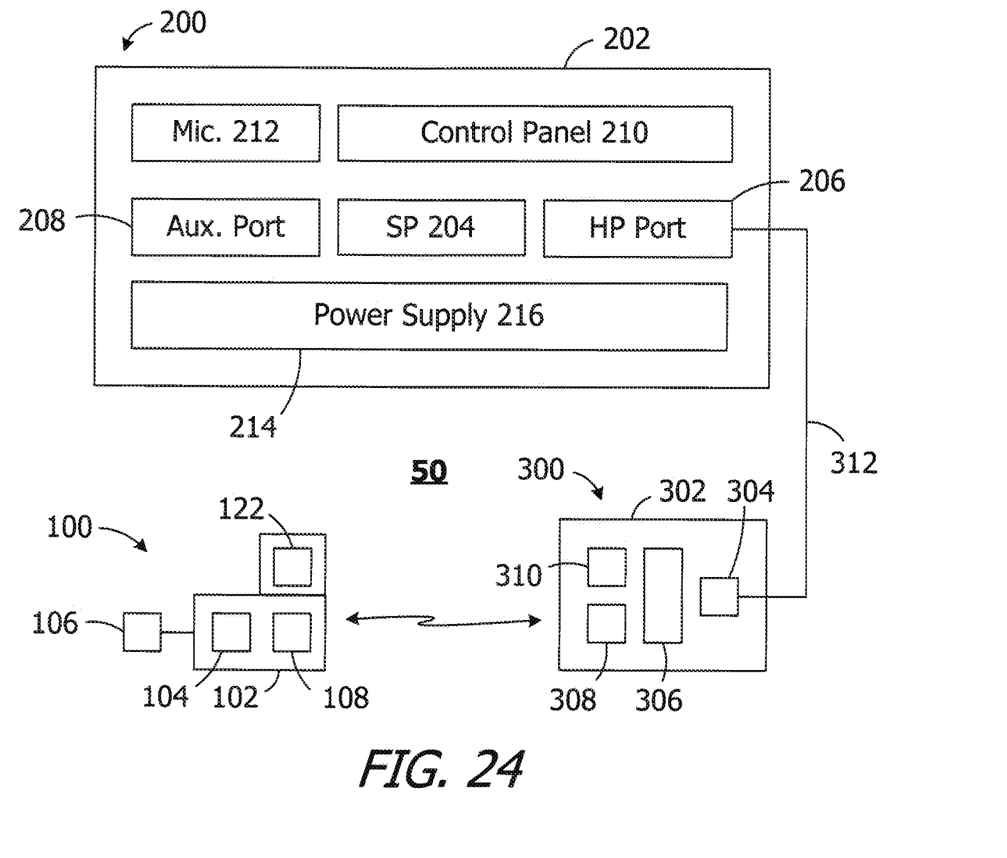
FIG. 24 is a diagrammatic view of an exemplary ICS system.

The present inventions have application in a wide variety of systems including, but not limited to, those that provide sound (i.e., either sound or a perception of sound) to the hearing impaired. One example of such a system is an ICS system where an external sound processor communicates with a cochlear implant. Turning to FIG. 24, the exemplary cochlear implant system 50 includes the cochlear implant 100, a sound processor, such as the illustrated body worn sound processor 200 or a behind-the-ear sound processor, and a headpiece 300.

As noted above with reference to FIG. 1, the exemplary cochlear stimulator 100 illustrated in FIG. 24 includes a flexible housing 102 formed from a silicone elastomer or other suitable material, a processor assembly 104, a cochlear lead 106 with an electrode array, an antenna assembly 108, and a magnet or other positioning element 122.

The exemplary body worn sound processor 200 includes a housing 202 in which and/or on which various components are supported. Such components may include, but are not limited to, sound processor circuitry 204, a headpiece port 206, an auxiliary device port 208 for an auxiliary device such as a mobile phone or a music player, a control panel 210, one or more microphones 212, and a power supply receptacle 214 for a removable battery or other removable power supply 216 (e.g., rechargeable and disposable batteries or other electrochemical cells). The sound processor circuitry 204 converts electrical signals from the microphone 212 into stimulation data. The exemplary headpiece 300 includes a housing 302 and various components, e.g., a RF connector 304, a microphone 306, an antenna (or other transmitter) 308 and a disk-shaped positioning magnet 310, that are carried by the housing. The headpiece 300 may be connected to the sound processor headpiece port 206 by a cable 312. The positioning magnet 310 is attracted to the magnet 120 of the cochlear stimulator 100, thereby aligning the antenna 308 with the antenna of the antenna assembly 108.

The stimulation data and, in many instances power, is supplied to the headpiece 300. The headpiece 300 transcutaneously transmits the stimulation data, and in many instances power, to the cochlear implant 100 by way of a wireless link between the antennas. The stimulation processor 128 (FIG. 1) converts the stimulation data into stimulation signals that stimulate the electrodes of the electrode array on the cochlear lead 106.

In at least some implementations, the cable 312 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 212 on the sound processor 200, the microphone 306 may be also be omitted in some instances. The functionality of the sound processor 200 and headpiece 300 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. By way of example, the inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. An antenna assembly for use with a medical implant, the antenna assembly comprising:
   an antenna that defines at least one turn; and
   an electromagnetic shield that extends around the antenna;
   wherein
   the antenna includes an electrically conductive antenna conductor that defines an antenna conductor resistance and an electrically conductive antenna sheath, over the electrically conductive antenna conductor, formed from a non-conductive elastomer that is dosed with electrically conductive particles and/or electrically conductive fibers and that defines an antenna sheath resistance that is greater than the antenna conductor resistance.

2. An antenna assembly as claimed in claim 1, wherein the electromagnetic shield includes an electrically conductive shield conductor that defines a shield conductor resistance and an electrically conductive shield sheath, over electrically conductive shield conductor, that defines a shield sheath resistance that is greater than the shield conductor resistance.

3. An antenna assembly as claimed in claim 1, wherein the electrically conductive antenna conductor consists of a single wire.

4. An antenna assembly as claimed in claim 1, wherein the antenna includes a plurality of electrically conductive antenna conductors and a respective plurality of electrically conductive antenna sheaths; and
   the electrically conductive antenna conductors and the electrically conductive antenna sheaths are located within a carrier that maintains the position of the electrically conductive antenna conductors in predetermined positions relative to one another.

5. An antenna assembly as claimed in claim 4, wherein each of the electrically conductive antenna conductors consists of a single wire.

6. An antenna assembly as claimed in claim 4, wherein each of the electrically conductive antenna conductors comprises a plurality of twisted wires.

7. An antenna assembly as claimed in claim 1, wherein the antenna is located within an overmolded antenna holder.

8. An antenna assembly as claimed in claim 7, wherein the electrically conductive antenna sheath comprises a portion of the overmolded antenna holder.

9. An antenna assembly as claimed in claim 1, wherein the electrically conductive antenna sheath is 5-30% electrically conductive particles and/or electrically conductive fibers.

10. An antenna assembly as claimed in claim 1, wherein the antenna sheath resistance is at least 10% greater than the antenna conductor resistance.

11. An antenna assembly as claimed in claim 1, wherein the antenna sheath resistance is 10 to 30% greater than the antenna conductor resistance.

12. A cochlear implant, comprising:
    a stimulation processor;
    a cochlear lead with an electrode array operably connected to the stimulation processor; and
    an antenna assembly as claimed in claim 1 operably connected to the stimulation processor.

13. An antenna assembly as claimed in claim 1, wherein the electrically conductive antenna conductor comprises drawn filled tubing.

14. An antenna assembly for use with a medical implant, the antenna assembly comprising:
    an antenna that defines at least one turn; and
    an electromagnetic shield that is wound around the antenna;
    wherein
    the electromagnetic shield includes an electrically conductive shield conductor that defines a shield conductor resistance and an electrically conductive shield sheath, over the electrically conductive shield conductor, that defines a shield sheath resistance that is greater than the shield conductor resistance.

15. An antenna assembly as claimed in claim 14, wherein the electrically conductive shield sheath comprises a non-conductive elastomer that is dosed with electrically conductive particles and/or electrically conductive fibers.

16. An antenna assembly as claimed in claim 15, wherein the electrically conductive shield sheath is 5-30% electrically conductive particles and/or electrically conductive fibers.

17. An antenna assembly as claimed in claim 14, wherein the shield sheath resistance is at least 10% greater than the shield conductor resistance.

18. An antenna assembly as claimed in claim 14, wherein the shield sheath resistance is 10 to 30% greater than the shield conductor resistance.

* * * * *